United States Patent [19]
Gray

[11] Patent Number: 5,388,576
[45] Date of Patent: * Feb. 14, 1995

[54] INFLATABLE RESUSCITATION DEVICE

[75] Inventor: Thomas C. Gray, Clarkston, Wash.

[73] Assignee: Grayco, Inc., Clarkston, Wash.

[ * ] Notice: The portion of the term of this patent subsequent to Apr. 26, 2011 has been disclaimed.

[21] Appl. No.: 106,286

[22] Filed: Aug. 13, 1993

Related U.S. Application Data

[63] Continuation-in-part of Ser. No. 951,984, Sep. 28, 1992, Pat. No. 5,305,739.

[51] Int. Cl.⁶ .............................................. A61M 15/00
[52] U.S. Cl. ........................... 128/205.13; 128/205.16; 128/205.25; 128/206.28; 417/473; 417/478; 417/389
[58] Field of Search ............... 417/473, 389, 478, 479, 417/480; 128/727, 728, 204.18, 203.11, 205.13, 205.16, 205.25, 206.21, 206.28, 202.28, 28

[56] References Cited

U.S. PATENT DOCUMENTS

| | | | |
|---|---|---|---|
| 3,063,620 | 11/1962 | Black | 417/478 |
| 3,356,100 | 12/1967 | Seeler | 137/512.4 |
| 4,521,166 | 6/1985 | Phillips | 417/478 |
| 4,536,136 | 8/1985 | Lan | 417/389 |
| 5,005,568 | 4/1991 | Loescher | 128/202.28 |
| 5,016,625 | 5/1991 | Hsu | 128/201.25 |
| 5,121,745 | 6/1992 | Israel | 128/202.28 |
| 5,133,344 | 7/1992 | Jurrius | 128/201.23 |
| 5,146,914 | 9/1992 | Sturrock | 128/203.11 |

*Primary Examiner*—Edgar S. Burr
*Assistant Examiner*—Eric P. Raciti
*Attorney, Agent, or Firm*—Frederick Gotha

[57] ABSTRACT

A pulmonary resuscitator is set forth of the type having a compressible bladder to be depressed to supply air to a mask. Both the compressible bladder and mask have integral therewith a network of inflatable tubes which when pressurized resiliently rigidify the bladder and mask to establish nominal erected bladder and mask shapes. The bladder has an inlet check valve and the mask has an outlet check valve where the outlet check valve utilizes a flapper valve for permitting flow of fluid into the mask upon depression of the bladder. Exhaust ports are located adjacent the flapper valve and are closed by the flapper valve when the bladder is depressed. The exhaust ports are opened when the flapper valve closes as the bladder returns to its nominal shape after being depressed. An air spring contained within the bladder chamber is in fluid communication with the network of inflatable tubes and through limiting orifices controls the rate at which the bladder returns to its nominal shape after depression.

6 Claims, 11 Drawing Sheets

INFLATABLE RESUSCITATION DEVICE

This is a Continuation-In-Part of U.S. patent application Ser. No. 07/951,984, filed Sep. 28, 1992, now U.S. Pat. No. 5,305,739.

FIELD OF THE INVENTION

This invention relates to an inflatable pulmonary resuscitator where both the face mask and bladder pump members which comprise the device are inflatable.

BACKGROUND OF THE INVENTION

Light weight portable general utility pumps suitable to inflate objects with a gaseous media, typically air, are very useful. One such application is a cardio-pulmonary resuscitator mouth-to-mouth pump and respirator.

In emergency cardio-pulmonary resuscitation mouth-to-mouth respiration is employed to restore cardiac output and pulmonary ventilation following cardiac arrest and apnea. Mouth-to-mouth resuscitation is a method of artificial ventilation involving an overlap of the patient's mouth with the operator's mouth to inflate the patient's lungs by blowing, followed by an unassisted expiratory phase brought about by elastic recoil of the patient's chest and lungs. Emergency mouth-to-mouth resuscitation requires this procedure to be repeated twelve to sixteen times a minute and therefore exposes a person administering the artificial respiration to disease. Thus, mouth-to-mouth cardiopulumonary resuscitation which generally is the first emergency aid available to a patient suffering from cardiac arrest exposes the person performing the mouth-to-mouth respiration to high risk of disease and therefore substantially inhibits the willingness of the person to administer such aid. Medical teams called to such emergencies have resuscitator apparatus which force gas, usually oxygen, into the lungs to produce the artificial ventilation; however, such devices are expensive and not generally available.

Mask devices have also been developed which may be placed over the nose and mouth of the patient; this permitted the administrator of the artificial respiration to blow air into the patient's lungs without mouth-to-mouth contact. Such masks, however, cannot be stored in a relatively small space such as a shirt or jacket pocket and thus are inconvenient to carry. Similarly, resuscitation apparatus comprising a ventilator mask and a manually collapsible gas receptacle such as the resuscitator disclosed in U.S. Pat. No. 5,067,487, likewise, cannot be carried easily in a shirt or jacket pocket because of the limitations inherent in the materials used in the construction of the apparatus.

SUMMARY OF THE INVENTION

In a preferred embodiment of this invention an inflatable bladder has along its outside a plurality of inflatable channels. Inlet valve means into the bladder admit air or oxygen. Exit valve means from the bladder allows for the discharge of the media under pressure. The bladder is omni-compressible, that is it can be compressed from any direction along its axis or normal to the axis. The inflatable channels once inflated act to retain the bladder in a predetermined shape and volume. Valve means into the channels permit their inflation.

Preferably the channels in this preferred embodiment have generally circular cross-sections with walls that fold over to begin the wall of an adjacent channel; the channel walls where they do so are sealed, preferably heat sealed, to the bladder wall. Thus, the bladder has an external wall that is also the external wall of the channels, and the channels are completed by side-by-side re-entrant walls that trace a serpentine path around the inside of the external bladder wall. This construction gives the bladder rigidity and resilience, so that it will readily go back to its predetermined shape after having gaseous media pumped from it by the action of compressing it in any direction. When compression is relieved, the bladder is again filled with the gaseous media from whatever source is desired. This construction provides a flexible bladder that self-erects into a predetermined shape because of the omnipresent positive erectile pressure in the channels. The construction has high integrity because of the side-by-side disposition of the channels and the outer channel wall provided by the outer wall of the bladder heat sealed to the re-entrant inner channel wall.

There is, therefore, provided according to the present invention, an improved pulmonary resuscitator where both the mask and bladder type pump are inflatable structures which can be stored in a relatively small storage space and therefore conveniently carried in a jacket or shirt pocket.

The present invention is directed to an improved pulmonary resuscitator of the type having a compressible bladder to be depressed to supply air to a mask device where the bladder has integrally contained therein an inflatable continuous fluid channel network which when pressurized resiliently rigidify the bladder to establish a nominal erected bladder shape. The bladder has an inlet check valve and the mask has an outlet check valve where the outlet check valve delivers air when the bladder is depressed and exhausts air from the mask as the bladder returns to its nominal erected shape. Having a construction similar to the bladder, the mask device is made of a flexible plastic material and has integral therewith a network of inflatable fluid channels. In one embodiment of the invention the inflatable fluid channels of the mask are in fluid communication with the network of inflatable channels contained in the bladder; and in another embodiment are separate fluid channels, but in either case, when pressurized, resiliently rigidify the mask to establish a nominal erected mask shape.

An inflatable air spring or biasing tube made of a flexible rubberized silk cloth material is integrally contained within the bladder and is in fluid communication with the inflatable channel network such that when the bladder is depressed air pressure within the bias tube will increase and upon release of the bladder will decrease thereby biasing the bladder to return to its nominal shape. To control the collapse rate of the bias tube, limiting orifices in the inflatable fluid channels in fluid communication with the bias tube are utilized to control the rate at which air will flow from the inflatable channels into the bias tube and from it. An inlet check valve is carried by the bladder which closes when the bladder is depressed. The air within the bladder is then permitted to exhaust through the outlet check valve of the mask. When the force compressing the bladder is released, the bias tube contributes to the rate at which the bladder will return to its original shape and because of the lower air pressure within the bladder chamber after being depressed, the inlet check valve will open to allow ambient air to enter into the bladder chamber.

In the preferred embodiment of this invention, the mask device contains inflatable fluid channels so disposed and arranged such that when the inflatable fluid channels are pressurized, they resiliently rigidify the mask device to establish a nominal erected mask shape. Integrally contained in the mask is a bladder connector portion having a plurality of exhaust ports and a flapper valve located at the inlet orifice of the bladder connector. The compressible bladder in the preferred embodiment has inflatable fluid channels which when pressurized resiliently rigidify the bladder to establish a nominal erected bladder shape; these inflatable fluid channels are separately pressurized from the mask device. The compressible bladder has an integral neck portion formed by inflatable fluid channels which comprise a part of the network of fluid channels. The neck portion is releaseably insertible into the bladder connector portion of the mask device where the neck portion of the bladder is sealingly held to permit relative rotation between the neck portion and bladder connector.

In another embodiment of the invention, the neck portion of the bladder and the bladder connector of the mask are integrally connected to form part of the network of the inflatable fluid channels such that both the mask and bladder fluid channels are in fluid communication and therefore when pressurized form the nominal bladder and nominal mask shapes.

Thus, an inflatable pulmonary resuscitator is provided where nominal bladder and mask shapes are achieved through pressurization of a network of interconnected fluid channels which when pressurized resiliently rigidify and form nominal bladder and mask shapes. The mask device is separately inflatable in one embodiment and has a bladder connector portion which is releasably and sealingly insertible into the neck portion of the bladder to permit the bladder to be rotated and angularly positioned with respect to the mask. The inflatable structure permits the resuscitator to occupy a very small space when deflated and therefore the device can be carried in a pocket, small bag or purse.

BRIEF DESCRIPTION OF THE DRAWINGS

These and other features and advantages will become appreciated as the same become better understood with reference to the following specification, claims and drawings wherein:

DETAILED DESCRIPTION

Figure 1:
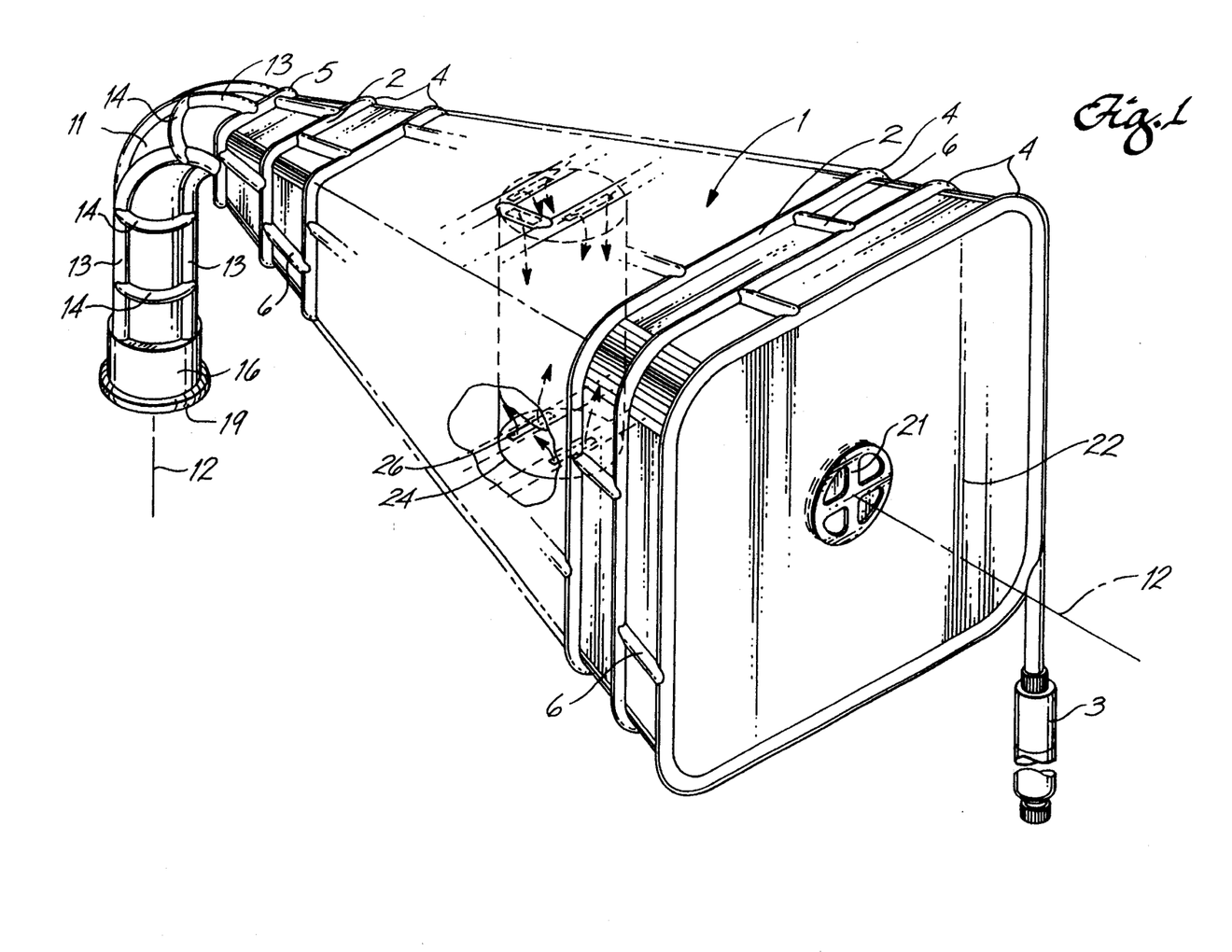
FIG. 1 is a perspective view of the compressible bladder of this invention illustrating the fluid channel network.
Figure 6:
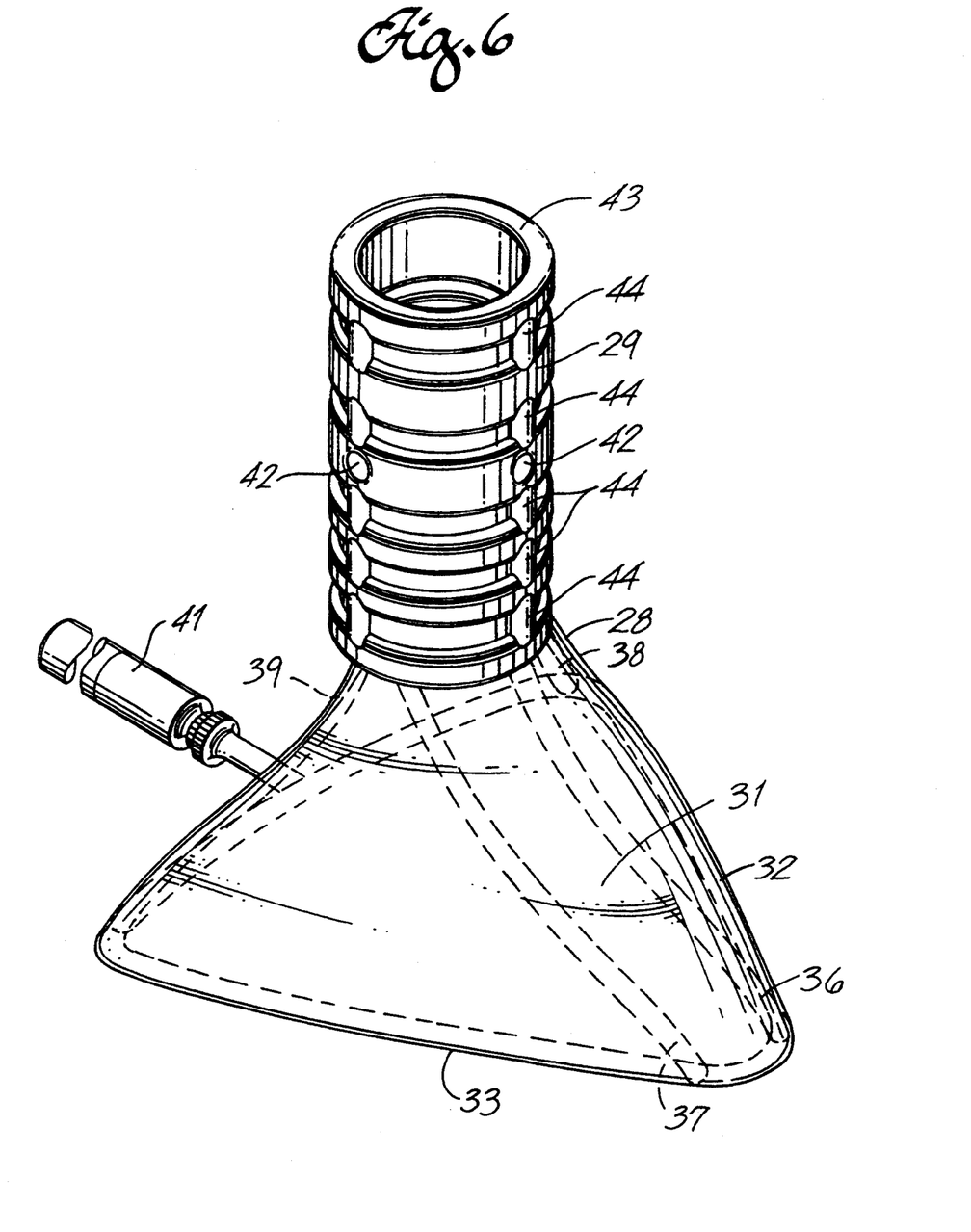
FIG. 6 is a perspective view of one embodiment of the mask device of this invention.
Figure 9:
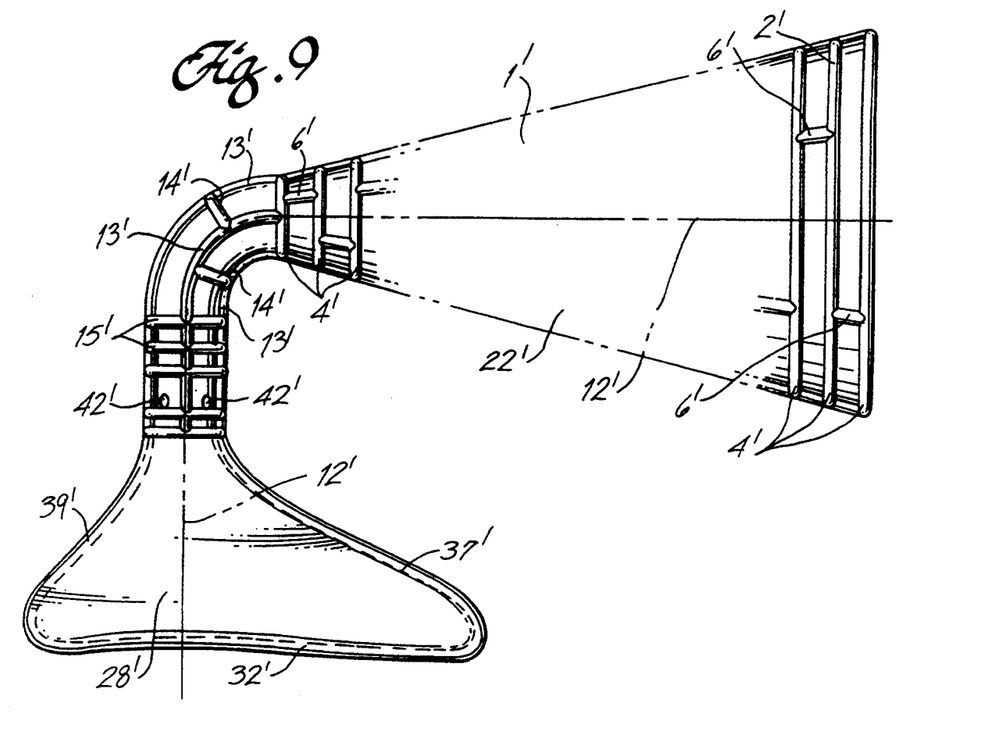
FIG. 9 is an illustration of another embodiment of this invention where the mask and bladder device are integrally connected.

The resuscitation instrument of this invention in the preferred embodiment consists of a bladder or pump member which is separately inflatable for insertion into a user or mask device which is also separately inflatable; the bladder or pump is illustrated in perspective in FIG. 1 and the mask device or user device is shown in perspective after being inflated in FIG. 6. Another embodiment of this invention is shown in FIG. 9 which depicts the resuscitator as a one-piece device having the bladder integrally connected to the mask or user device.

Figure 5:
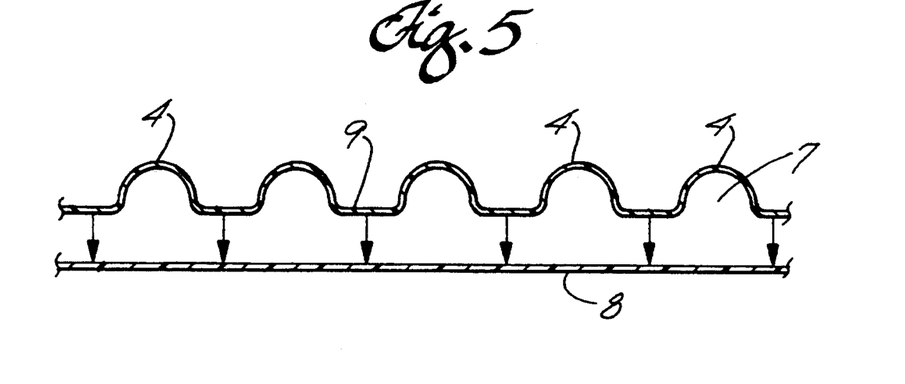
FIG. 5 is a partial cross-sectional view illustrating a joining of materials in the formation of the fluid channels integrally contained in the mask and bladder devices of this invention.

Referring to FIG. 1, the bladder 1 is shown in its nominal erected bladder shape after the network of fluid channels 2 have been pressurized by air which had been stored under pressure in compressed air cannister 3. As can be seen in FIG. 1, the network of fluid channels 2 consists of a plurality of substantially parallel rib members 4 which are in fluid communication with each other through a plurality of axial bridge struts 6 interconnecting the rib members 4. The rib members 4 and the axial bridge struts 6 are integrally formed in a thin grade plastic which is extremely flexible such as a rubberized silk or rubberized cloth or of a rayon or nylon type material. By referring to FIG. 5 the method of construction of the rib members 4 and axial bridge struts 6 is illustrated. As can be seen in FIG. 5, the fluid channel 7 is formed by utilizing two sections of rubberized cloth 8 and 9 which may be sewn together to form the air channels 7 or sealed with heat and pressure by methods which are well known in the prior art. Thus, in the construction of bladder member 1, there is a continuous outer surface and continuous inner surface each made of thin, flexible rubberized cloth which, when the rib members and axial bridge struts are pressurized, resiliently rigidify the form of the bladder shape.

Figures 2, 3:
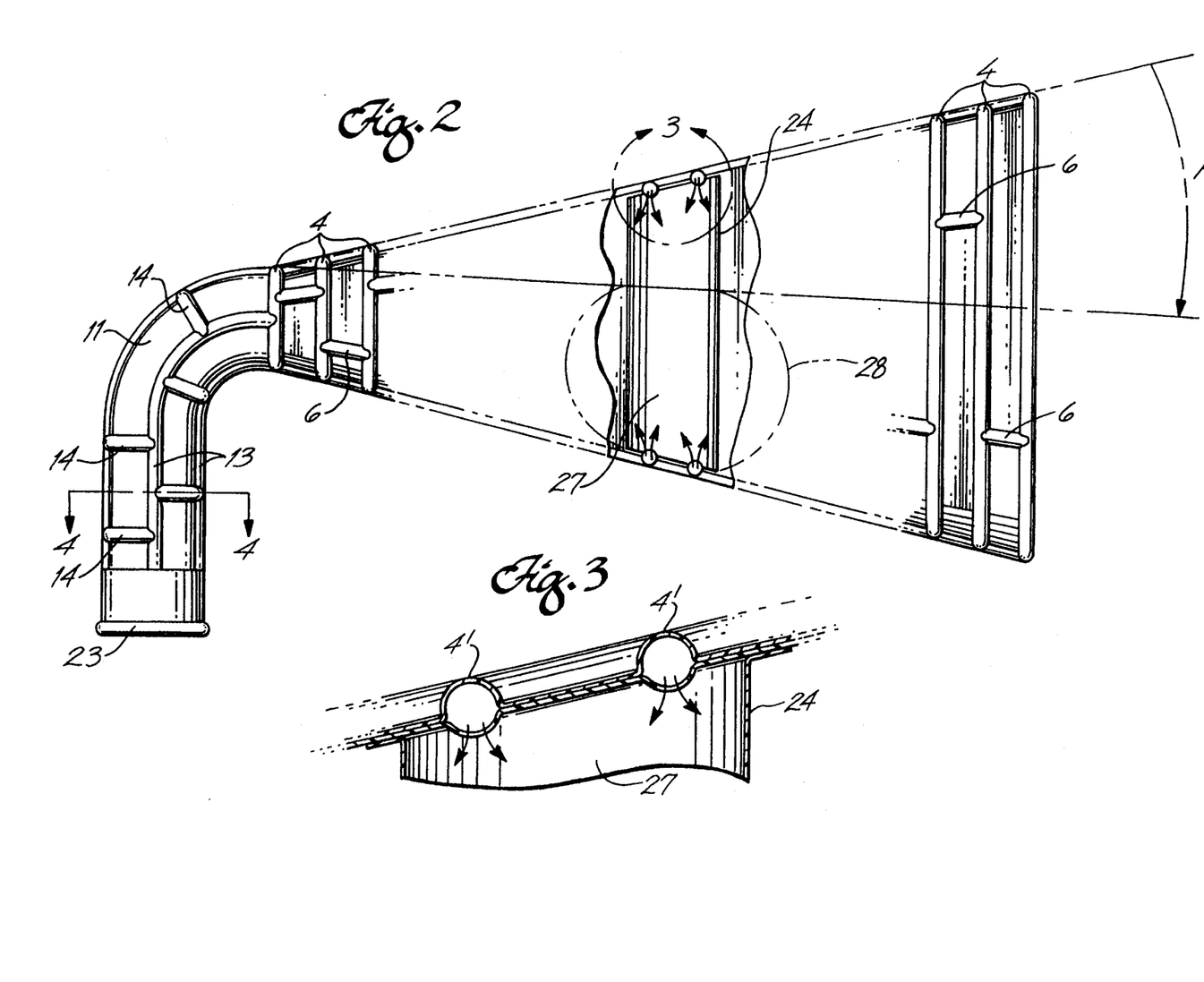
FIG. 2 is a part broken, side elevational view of FIG. 1.
FIG. 3 is an exploded cross-sectional view of the area 3 shown in FIG. 2.
Figure 4:
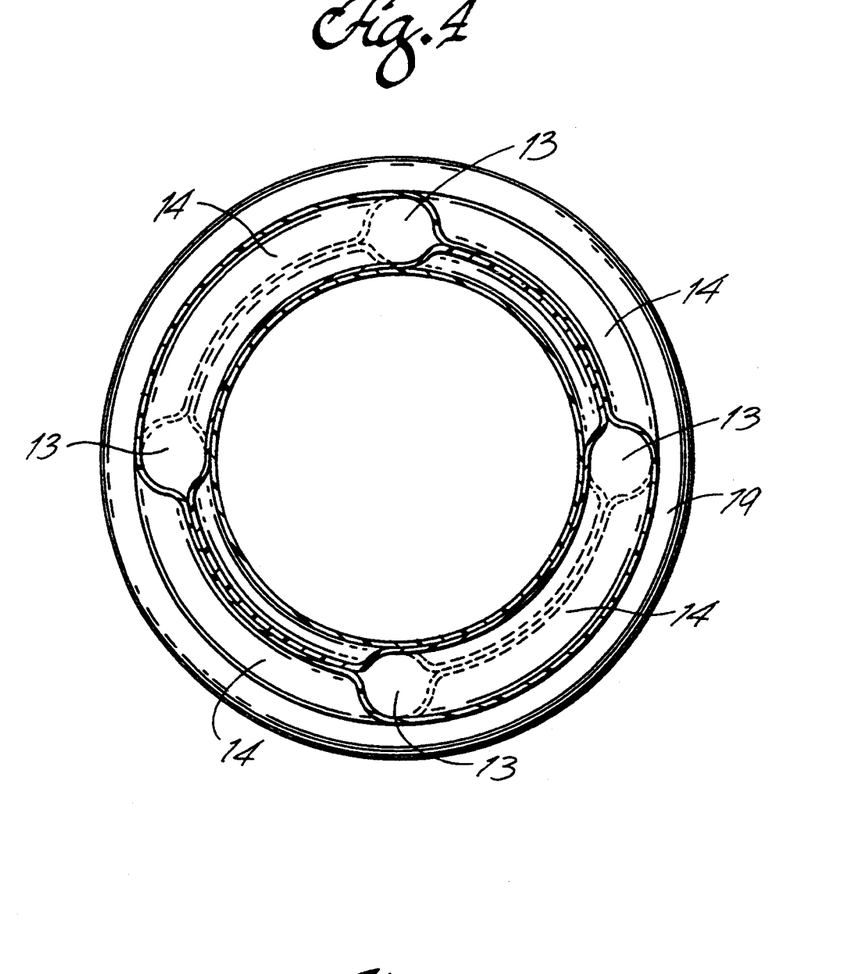
FIG. 4 is a cross-sectional view taken along the line 4—4 of FIG. 2.

A connector portion 11 is shown in FIGS. 1 and 2 integrally formed with bladder 1 and extending axially along axis of elongation 12. Connector 11 is of the same construction as bladder 1 and as can be seen in FIGS. 1 and 2, has a plurality of axially extending fluid channels 13 which are in fluid communication with the distal rib 5 at which the bladder transitions into connector portion 11. Axially extending fluid channels 13 are in fluid communication with bridge struts 14 which radially interconnect fluid channels 13. Thus, the network of fluid channels and bridge struts, when pressurized, form the connector portion shape and resiliently rigidify the connection portion when pressurized to form a nominal shape for the connector portion of the bladder. As in the bladder construction, the connector portion is formed by sewing or sealing with heat and pressure rubberized cloth 8 and 9 (refer to FIG. 5) to form the outside and inside surfaces of the connector portion and the air channel 7. By referring to FIG. 8b, the distal cap 16 of the connector portion can be seen releasably and captively held by mask connector 17. The distal cap has inflatable rings 18 which are in fluid communication with axially extending fluid channels 13 and bridge struts 14 forming arcuately shaped ribs which form a cylindrical cap shape; at the distal tip of cap 16, connector ring 19 extends radially beyond inflatable rings 18 forming a lip for enhancing the releasable seal between connector portion 11 and mask connector 17 after the connector portion is inserted into the mask connector.

A inlet check valve 21 is show in FIG. 1 carried in the surface 22 of the bladder at its proximate end. When the bladder is depressed by external force, the air pressure in chamber 22 will increase and close inlet check valve 21; thus, the air contained within the chamber will be forced through the connector portion 11 of the bladder and exhausted through opening 23 located in the distal cap 16 of connector portion 11.

By referring to FIGS. 1, 2 and 3 an air spring or bias tube 24 can be seen which controls the rate at which the bladder 1 after being depressed resumes its nominal shape. In the preferred embodiment shown in FIGS. 1 and 2, air spring 24 has a cylindrical shape and may be made of the rubberized silk cloth material used in the construction of the bladder and the connector portion of the bladder. To control the rate of return of the bladder 1 to its nominal shape, limiting orifices 26 are in fluid communication with rib members 4 and axial bridge struts 6. When bladder 1 is compressed as shown by arrow (A) in FIG. 2, air spring 24 will be compressed and bulge as a result of the increased pressure within air spring chamber 27 causing the air spring to expand as shown in phantom 28. The limiting orifices are so constructed and designed to permit the network of fluid channels forming the structure of the bladder to return to their nominal shape quickly; during the return to nominal shape, inlet check valve 21 will open and ambient air which is at a greater pressure then the pressure within chamber 22 will fill chamber 22 and check valve 21 will close when the pressure is equalized. Thus, not only does air spring 24 control the rate at which ambient air will fill the bladder 1, it will also act to stabilize the shape of the network of fluid channels. The construction of air spring 24 is more clearly shown in FIG. 3 which is an enlargement of area 3 shown on FIG. 2. In referring to FIG. 3, ribs 4' are in fluid communication with air spring chamber 27 to permit air spring chamber 27 to be pressurized with air simultaneously with the pressurization of the fluid channel network. Thus, when the bladder is compressed in the direction of arrow (A) as shown in FIG. 2, the pressure will increase within air spring chamber 27 above the equilibrium pressure of the fluid channel network when the bladder is depressed from its nominal shape; when the depressing force is removed the air spring will return to the equilibrium shape and the rate at which it will return to the equilibrium shape will be determined by the dimensions of limiting orifices 26.

By referring to FIG. 6, the preferred embodiment of the mask device of this invention can be seen in perspective. Mask device 28 is composed of two integrally connected portions, namely, a mask connector receptacle portion 29 and a face portion 31. As in the bladder construction, the mask device is shaped by a network of fluid channels which are in fluid communication such that when pressurized form the mask connector portion nominal shape and the nominal shape of the face portion 31. A triangularly shaped fluid channel or rib 32 is integrally formed in a clear flexible plastic material which is used for constructing the face portion 31. This permits the user of the resuscitation device to see the patient's face when administering resuscitation. The cavity 33 of the face portion 31 of the mask device communicates with mask connector 29 to permit air which is pumped from the bladder to flow to the patient. A flapper valve 34 is shown in FIGS. 10(A) and 10(B) which in the preferred embodiment is located in the mask connector or receptacle 29 and which functions so as to permit air flow into the face portion 31 of the mask device when the bladder 1 is compressed, and to close when the bladder depressing force is released. Referring again to face portion 31 as shown in FIG. 6, triangularly shaped rib 32 is interconnected to and in fluid communication with rib spars 36 and 37 which when pressurized resiliently rigidify the mask shape; similarly, lateral ribs 38 and 39 are in fluid communication with triangularly shaped rib 32 and rib spars 36 and 37 and form the network structure of the shape of the face portion 31 of the mask device. The mask device is separately inflatable from the bladder by compressed air canister 41.

Figure 7:
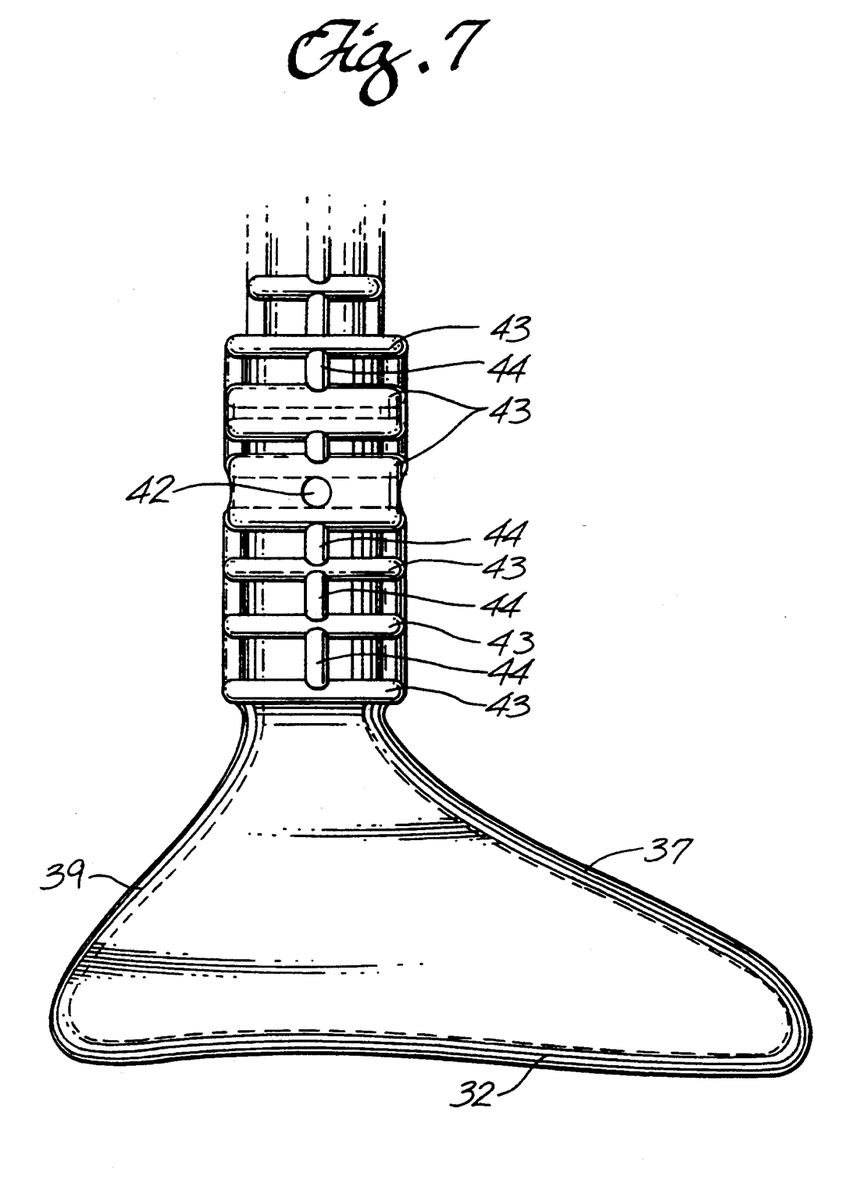
FIG. 7 is a left side elevation view of FIG. 6.
Figure 8A:
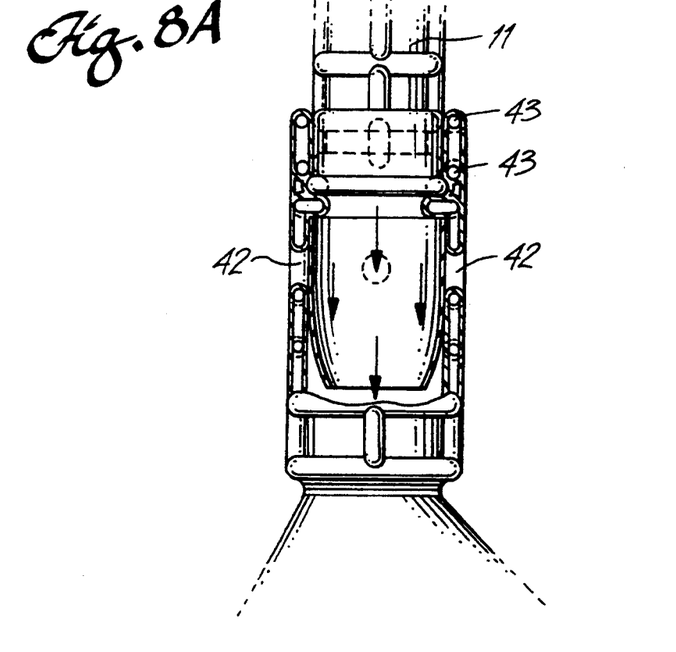
FIG. 8A is an illustration of a flapper valve contained in the connector portion in an open position.
Figure 8B:
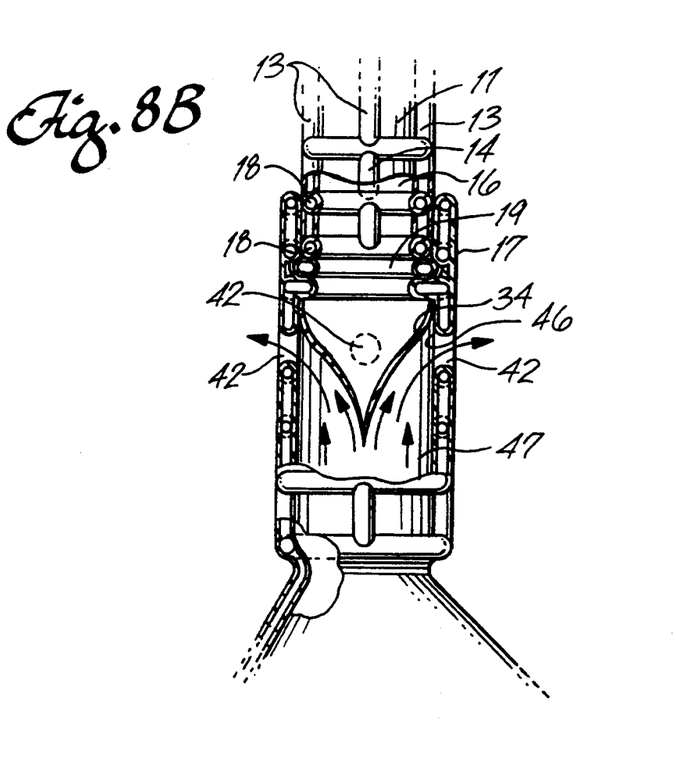
FIG. 8B is an illustration of the flapper valve shown in FIG. 8A in a closed position.

In FIG. 6, the mask connector or receptacle is shown in perspective. To exhaust exhaled air from the patient, mask connector 29 has a plurality of exhaust ports 42. By referring to FIGS. 7, 8(A) and 8(B) the structure of mask connector 29 can be seen. Referring to FIG. 7, inflatable mask rings 43 are shown to be interconnected through a plurality of bridge struts 44 which provide fluid communication between rings 43; and through rings 43 the struts are in fluid communication with rib spars 36 and 37 and lateral ribs 38 and 39. Flapper valve 34 may be bonded or sewn to the inner wall 46 which forms the boundary of the conduit cavity 47 contained within mask connector or receptacle 29. As can be seen in FIGS. 8(A), 8(B), 10(A) and 10(B), flapper valve 34 is made of a thin latex-type material which collapses against itself when air is sucked through conduit cavity 47 by the relative vacuum caused by bladder 1 returning to its nominal position after being depressed; the sucked air exhausting through exhaust ports 42 when flapper valve 34 is collapsed upon itself. Referring to FIGS. 8(A) and 10(A), when the bladder 1 is compressed, air is pumped from the bladder under pressure and the flapper valve opens thereby closing exhaust ports 42 and permitting air flow into the mask. In the preferred embodiment, the flapper valve is made of a flexible material such as plastic, rubber, cloth or a combination of these and less than 10 mm in thickness.

Figure 10:
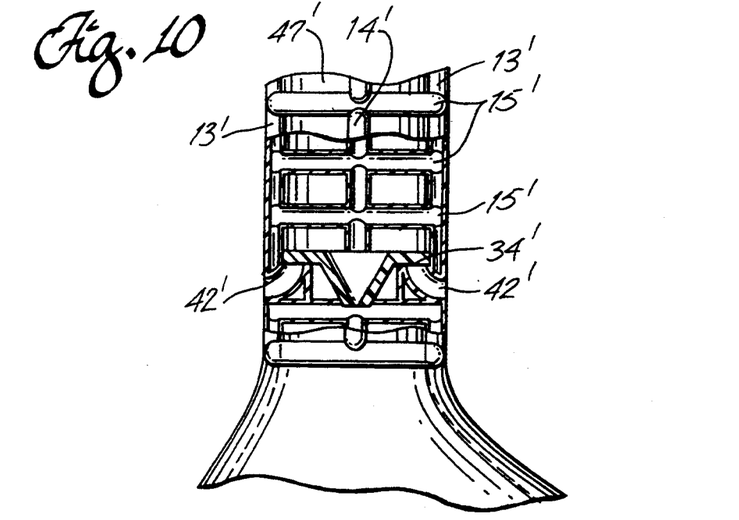
FIG. 10 is a partial cross-sectional view of FIG. 9 illustrating the outlet check valve controlling air flow into and from the mask device.
Figure 10A:
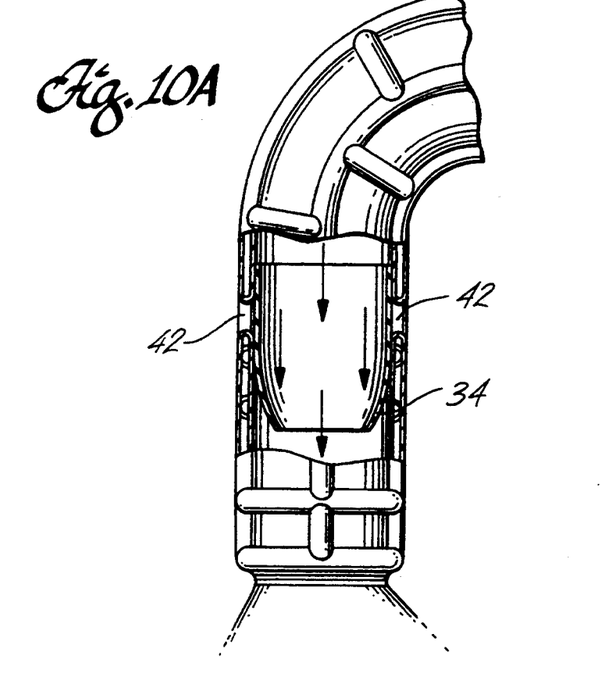
FIG. 10A is a preferred outlet check valve of this invention and is shown in an open position.
Figure 10B:
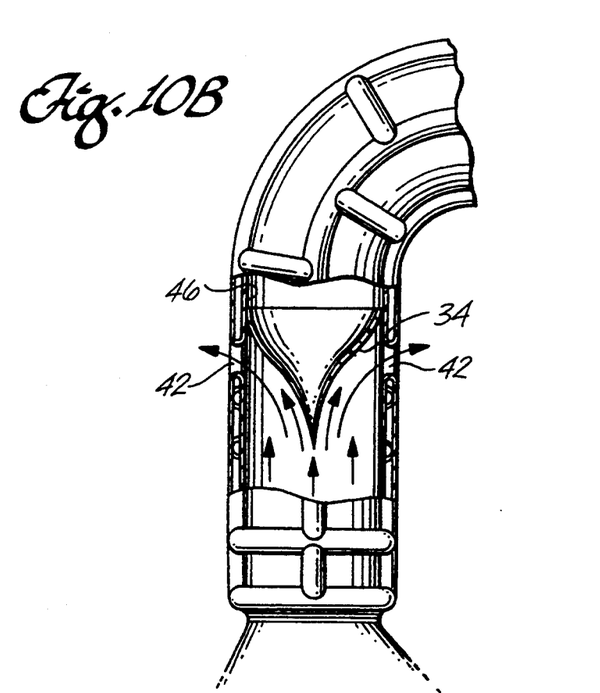
FIG. 10B is the preferred outlet check valve shown in a closed position.

Another embodiment of this invention is disclosed in FIGS. 9 and 10. In this embodiment, the bladder 1' and the mask device 28' are integrally joined together to form a one-piece resuscitation device. As in the embodiment above-described, this embodiment comprises a network of fluid channels 2' which are in fluid communication with each other and when pressurized resiliently ridigify to establish a nominal erected bladder shape and a nominal erected mask shape. The network of fluid channels 2' is composed of a plurality of rib members 4' and axial bridge struts 6' where the resuscitator device illustrated in FIG. 9 has an axis of elongation 12'. The method of construction of rib members 4' and axial bridge struts 6' in this embodiment is identical to the method of construction utilized in the preferred embodiment which is illustrated in FIG. 5. Referring again to FIG. 9, the connection transition between the bladder 1' and the mask 28' has axially extending fluid channels 13' and bridge struts 14' which are in fluid communication with rib spars 37' and 39'. Axially extending fluid channels 13' extend to and become integrally part of bridge spars 36' and 37' and lateral ribs 38' and 39' which in turn are in fluid communication with the triangularly shaped rib 32' that forms the bearing surface for the mask device. A plurality of inflatable rings 15' are in fluid communication with axially extending fluid channels 13' and are interconnected by inflatable bridge struts 14' such that upon pressurization form a transition structure from the bladder 1' to the mask 28.' Conduit cavity 47' is contained within the transition structure for directing air which has been pumped from bladder 1' to the mask 28'. An exhaust shuttle flapper valve is positioned intermediate the bladder 1' and mask device 28' to control the flow of air to the mask. Exhaust ports 42' are located adjacent the flapper valve and are closed when air is forced through conduit cavity 47' towards the mask 28' and are open to exhaust air from the patient as the bladder 1' returns to its original nominal shape after being depressed. After the bladder 1' is released, the nominal bladder shape is biased by an internal air spring or bias tube (not shown in FIG. 9) in the same manner as bias tube or air spring 34 described in the preferred embodiment of FIG. 1 returned the bladder to its nominal shape; this creates a vacuum and sucks ambient air back into the air chamber 22'. To effectively administer artificial respiration, the resuscitator must refill with air in approximately five seconds or less and should contain approximately 1.8 liters of air.

With reference to FIGS. 10 through 13 the presently preferred pump 56 is shown. The pump consists of a bladder 62 that is embraced around its girth by longitudinal channels 64.

Figure 12:
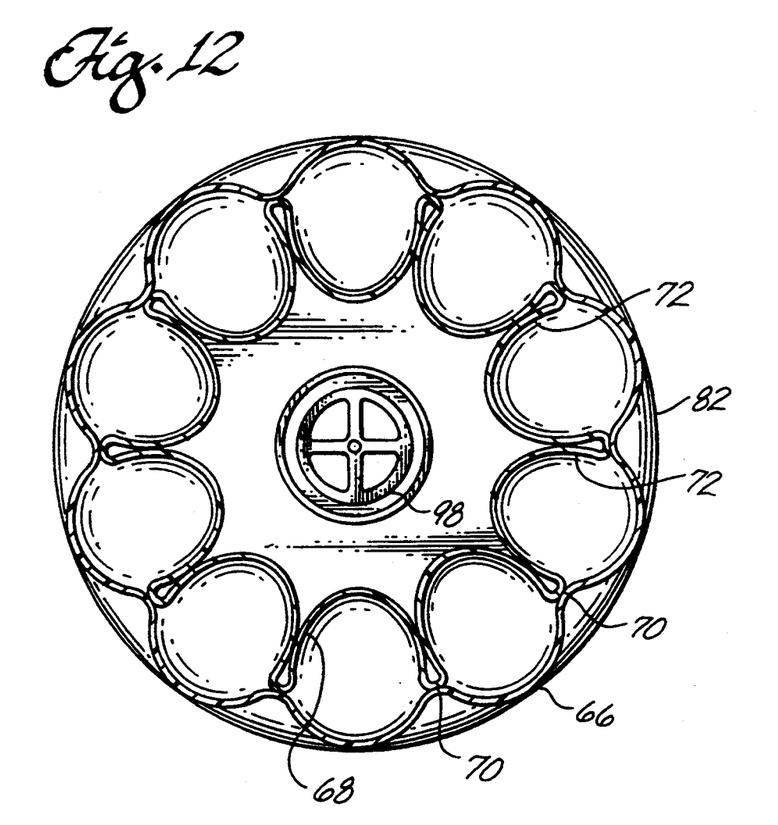
FIG. 12 is a cross-sectional view taken along the line 12—12 of FIG. 11.

As can be seen in FIG. 12, the channels are defined by an outer wall 66 and an inner wall 68. Inner wall 68 traces a serpentine path around the inside of wall 66 meeting it at reentrant points 70 where the walls are heat sealed together to form longitudinal bands of high integrity. The cross-section of the channels when inflated are essentially circular. Channel wall 68 touches itself regularly at 72. The circular cross-section and the inter channel resistance effected through these contacts at 72 provide very effective resilience and readily return the bladder to its predetermined shape after it has been depressed and during its refilling with a gaseous medium.

Figure 11:
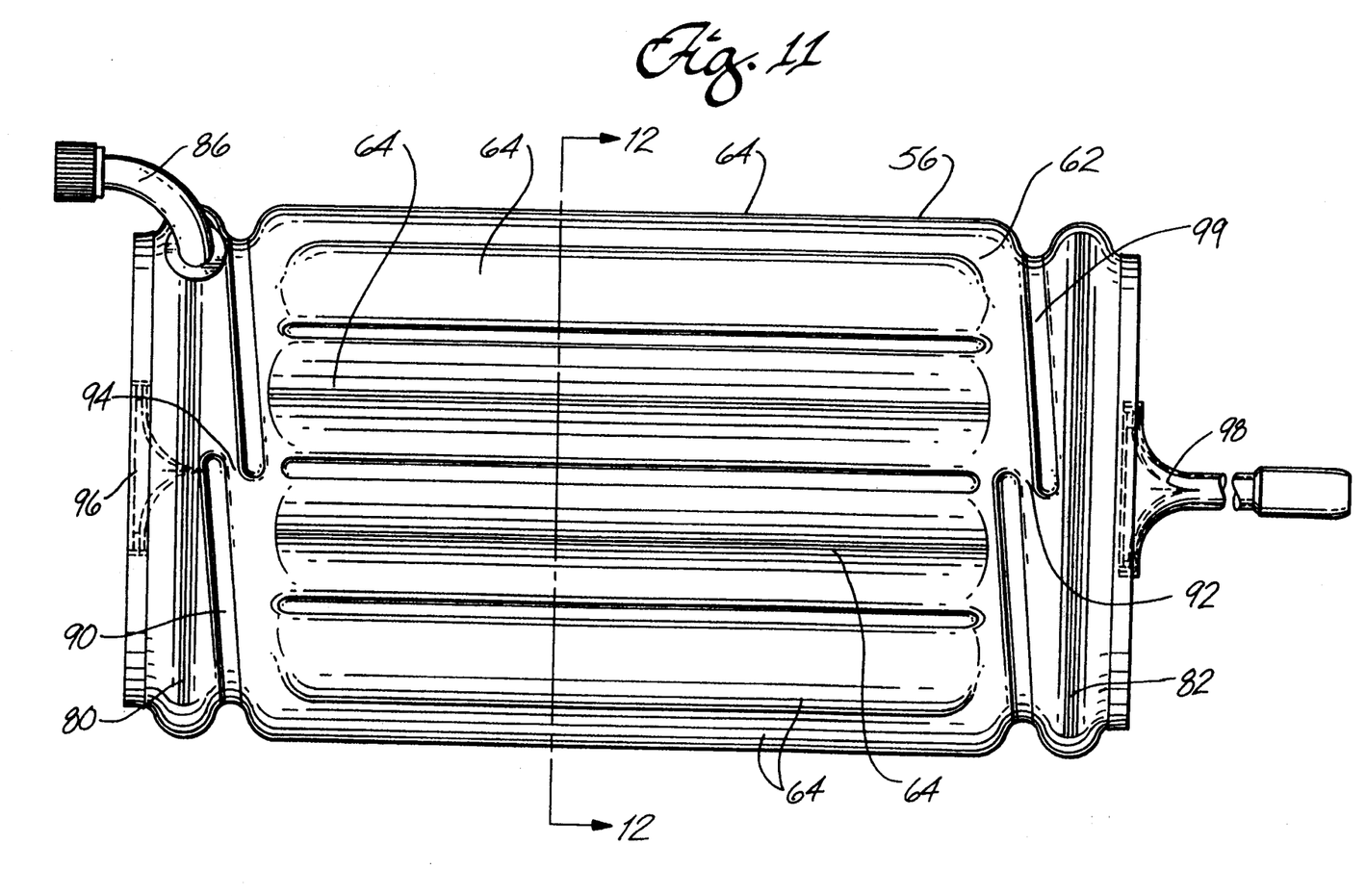
FIG. 11 is a side elevation of the presently preferred embodiment of this invention.

FIG. 11 also shows headers that communicate with the channels. These headers 80 and 82 provide for the inter channel communication.

An inlet valve and stem 86 into header 80 permits inflation of the channels.

Figure 13:
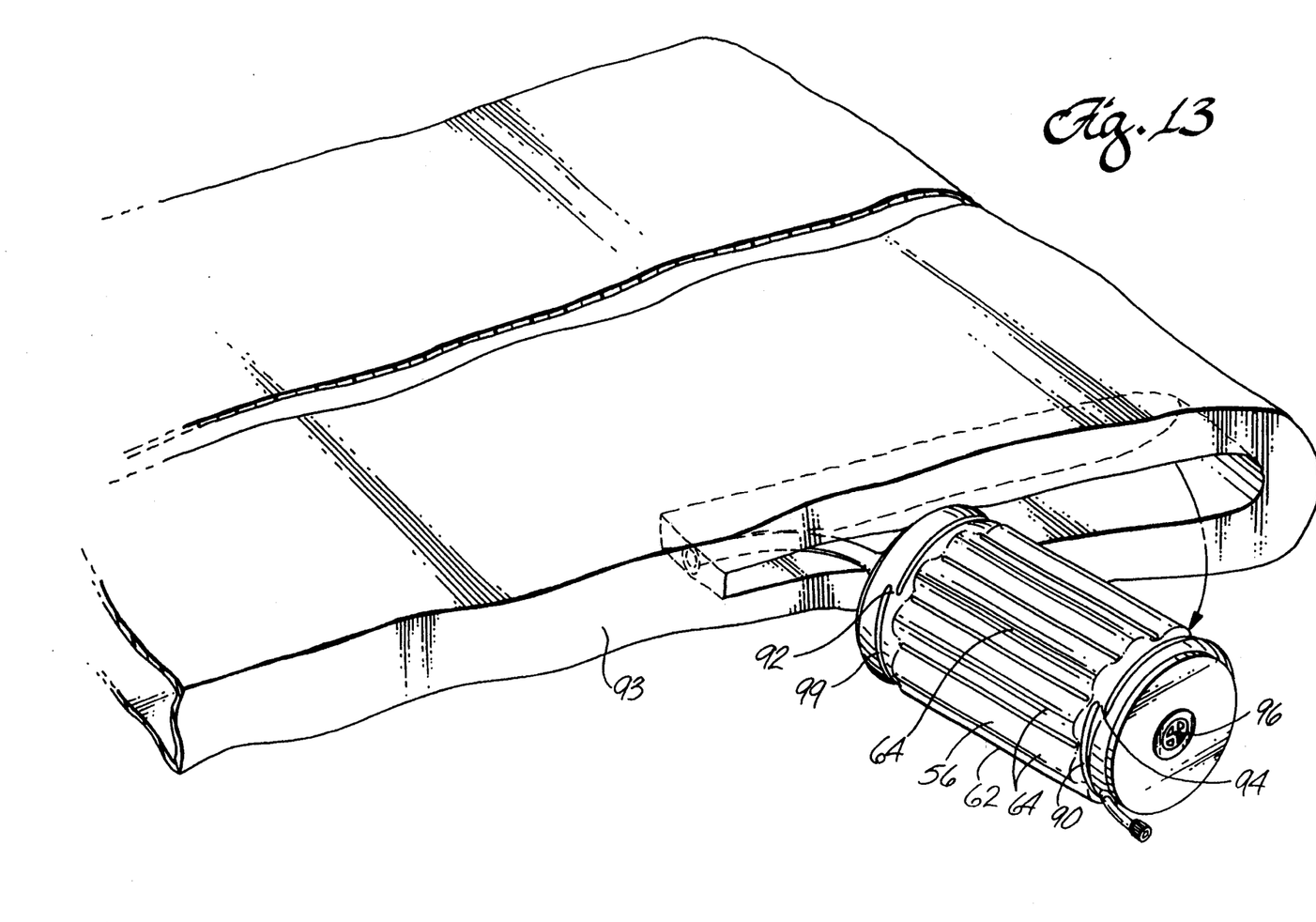
FIG. 13 shows this embodiment being used to fill an air pillow.

The headers have as an outer wall the outer wall of the bladder and as their inner wall an extension of the inner wall material of the channels. The headers have heat sealed bands 90 and 99 joining their inner and outer walls. A slight gap 94 in band 90 permits gas to pass from header 88 into the channels. The bladder has an outlet valve 98 that can be attached to a user device such as a resuscitator. FIG. 13 shows the bladder 60 being used in a more general way such as a pump for an air pillow 93.

Completing the description of the preferred bladder, a one way inlet check valve 96 into the interior of the bladder provides for the admission of the gaseous media. This valve is sandwiched between the plastic fabric at the end of the bladder in a in which the inlet valve resides. The inlet valve is heat welded to his fabric to secure it in place.

Thus, a device has been described which is made of a thin medical grade plastic that is extremely flexible. An integral network of interconnected air passageways has been presented which when pressurized by a compressed air cylinder, resiliently rigidify both the bladder and the mask to establish nominal shapes. The resuscitator of this invention does not require ambient air pressure to return the bladder and mask to their original shapes; this is achieved in one embodiment by utilizing an internal air spring or bias tube which is in fluid communication with certain rib members and the axial bridge struts between those members. The air struts and ribs contain limiting orifices which control the rate at which the bladder and mask return to their original shapes and in so doing cause a vacuum to occur in the bladder air chamber. The quick recovery cycle provided by the air spring allows the resuscitator to be used for emergency resuscitation.

While I have shown and described certain embodiments of the present safety valve device, it is to be understood that it is subject to many modifications without departing from the spirit and scope of the claims as recited herein.

What is claimed is:

1. A pulmonary resuscitator comprising in combination:
   (a) a pump for a fluid media comprising, a compressible bladder having a flexible wall and having a cavity therein enclosed by said flexible wall, inlet check valve means carried by said bladder for unidirectionally permitting passage of said fluid media into said cavity, a first network means comprising interconnected inflatable fluid channels integrally contained in said flexible wall, said first network means for inflatably erecting said compressible bladder and maintaining said bladder erect and resilient during compression of said bladder, valve means carried by said bladder for charging said first network means with a fluid and sealingly retaining said fluid within said first network during compression of said bladder, and inflatable bias means disposed within said bladder and in exclusive fluid communication with said first network means for biasing said bladder to retain a predetermined bladder shape during compression of said bladder, and
   (b) a user device to be fitted over the face of the person to be revived comprising a thin wall body made of a flexible material, a second network of interconnected inflatable fluid channels integrally contained within said thin wall body where said second network of fluid channels when inflated erect said thin wall body into a face mask shape and maintain said thin wall body erect and resilient, a third network of interconnected inflatable fluid channels integrally contained within said thin wall body and integrally connected with the said second network of inflatable fluid channels where said third network inflates upon inflation of said second network and when inflated erects and maintains a receptacle extending from said face mask to permit the passage of air to the users, and means carried by said thin wall body for inflating said second and third networks of inflatable fluid channels with a fluid and sealingly retaining said fluid within said second and third inflatable fluid channels.

2. The combination recited in claim 1 wherein said inflatable bias means includes a limiting orifice in exclusive fluid communicating with said first network of interconnected inflatable fluid channels to maintain said bladder erect and resilient during the compression of said bladder.

3. A pump for a fluid media for use with a user device comprising:
 (a) a pump for a fluid media comprising, a compressible bladder having a flexible wall and having a cavity therein enclosed by said flexible wall, inlet check valve means carried by said bladder for unidirectionally permitting passage of said fluid media into said cavity, outlet check valve means carried by said bladder for unidirectionally permitting passage of said fluid media from said cavity to said user device, a first network means comprising interconnected inflatable fluid channels integrally contained in said flexible wall, said first network means for inflatably erecting said compressible bladder and maintaining said bladder erect and resilient during compression of said bladder, valve means carried by said bladder for charging said first network means with a fluid and sealingly retaining said fluid within said first network during compression of said bladder, and inflatable bias means disposed within said bladder and in exclusive fluid communication with said first network means for biasing said bladder to retain a predetermined bladder shape during compression of said bladder;
 said user device further comprising:
 (a) a thin wall body made of a flexible plastic material;
 (b) a second network of interconnected inflatable fluid channels integrally contained within said thin wall body where said network of fluid channels when inflated erect said thin wall body into a face mask shape and maintain said thin wall body erect and resilient;
 (c) a receptacle member extending from said face mask to permit the passage of air to the user;
 (d) means carried by said thin wall body for inflating said second network of inflatable fluid channels with a gas and sealingly retaining said gas within said second network of inflatable fluid channels.

4. The pump recited in claim 3 wherein said inflatable bias means includes a limiting orifice in exclusive fluid communicating with said first network of interconnected inflatable fluid channels to maintain said bladder erect and resilient during the compression of said bladder.

5. An inflatable face mask for use in pulmonary resuscitation comprising:
 (a) a thin wall body made of a flexible plastic material;.
 (b) a second network of interconnected inflatable fluid channels integrally contained within said thin wall body where said network of fluid channels when inflated erect said thin wall body into a face mask shade and maintain said thin wall body erect and resilient;
 (c) a receptacle member extending from said face mask to permit the passage of air to the user;
 (d) means carried by said thin wall body for inflating said second network of inflatable fluid channels with a gas and sealingly retaining said gas within said second network of inflatable fluid channels.

6. An improved pulmonary resuscitator of the type having a compressible bladder to be compressed to supply air to a user device, said bladder having a flexible wall and an inlet check valve and said user device having an outlet check valve, wherein the improvement comprises:
 (a) a first network means comprising substantially orthogonal interconnected inflatable fluid channels integrally contained in said flexible wall said first network means upon inflation erecting said bladder and maintaining said bladder erect and resilient during compression of said bladder;
 (b) means carried by said bladder for inflating said first network of inflatable fluid channels with a gas and sealingly retaining said gas within said network during compression of said bladder.

* * * * *